United States Patent [19]
Scotti

[11] Patent Number: 5,213,575
[45] Date of Patent: May 25, 1993

[54] TWO-PIECE RETRIEVABLE CATHETER FORMING STRAIGHT AND T-SHAPE CONFIGURATIONS

[76] Inventor: Daniel M. Scotti, 720 Redmen Ave., Haddonfield, N.J. 08030

[21] Appl. No.: 496,440

[22] Filed: Mar. 20, 1990

[51] Int. Cl.⁵ .................... A61M 37/00; A61M 25/00
[52] U.S. Cl. ...................................... 604/95; 604/284
[58] Field of Search ............................... 604/280–284, 604/95, 264, 51, 53, 54

[56] References Cited

U.S. PATENT DOCUMENTS

| | | | |
|---|---|---|---|
| 3,119,392 | 1/1964 | Zeiss | 604/95 |
| 3,833,940 | 9/1974 | Hartenbach . | |
| 3,835,863 | 9/1974 | Goldberg et al. . | |
| 3,924,633 | 12/1975 | Cock et al. | 604/95 |
| 4,072,153 | 2/1978 | Swartz . | |
| 4,142,528 | 3/1979 | Whelan, Jr. et al. . | |
| 4,245,624 | 1/1981 | Komiya | 604/95 |
| 4,248,224 | 2/1981 | Jones . | |
| 4,309,994 | 1/1982 | Grunwald . | |
| 4,547,187 | 10/1985 | Kelly . | |
| 4,654,032 | 3/1987 | Morales-George . | |
| 4,675,008 | 6/1987 | Tretbar . | |
| 4,740,195 | 4/1988 | Lanciano | 604/95 |
| 4,748,984 | 6/1988 | Patel . | |
| 4,758,221 | 7/1988 | Jureidini | 604/95 |
| 4,781,682 | 11/1988 | Patel | 604/280 |
| 4,807,626 | 2/1989 | McGir | 604/281 |
| 4,824,435 | 4/1989 | Giesy et al. | 604/280 |

OTHER PUBLICATIONS

Catalogue of Catheters and Accessories from American Cystoscope Makers, Inc., 1960, p. 64.
"Percutaneous Cholecystostomy", *Percutaneous Biliary Decompression*, p. 13.35.
"T-Tube Replacement", *Interventional Biliary Radiology*, pp. 265–276.
"T-Tube Replacement", *The Hepatobiliary System*, pp. 743–744.

*Primary Examiner*—C. Fred Rosenbaum
*Assistant Examiner*—Mark Bockelman
*Attorney, Agent, or Firm*—Lerner, David, Littenberg, Krumholz & Mentlik

[57] ABSTRACT

A retrievable two piece catheter for percutaneous insertion into the common bile duct or similar vessel or canal of a patient is disclosed. The catheter is introduced as a single unit over a cannula and then formed in-situ within the duct into a T-tube configuration. Two sutures threaded through a main catheter are attached to a shorter distal auxiliary catheter, one in the center of the auxiliary catheter and one at an end thereof. After the two piece catheter has been inserted to the desired location and the cannula removed, the sutures are manipulated to maneuver the auxiliary catheter until it lies generally perpendicular to the elongated main catheter to thereby form the T-tube in fluid communication with each other. A suture-locking device provides self-retaining characteristics and the T-tube catheter can be easily retrieved, repositioned or exchanged. The T-tube catheter can be modified within a long distal limb to stent the Ampulla of Vater after balloon sphincteroplasty. A second type of two piece catheter with a self-retaining loop can be used as an internal biliary drainage catheter when treating distal common bile duct obstructions.

28 Claims, 3 Drawing Sheets

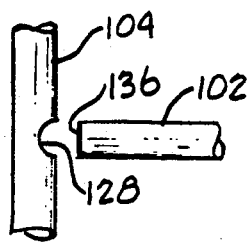 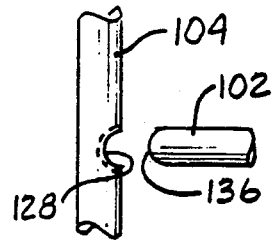 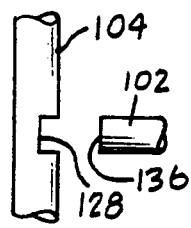 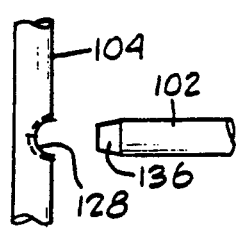
FIG. 4A  FIG. 4B  FIG. 4C  FIG. 4D
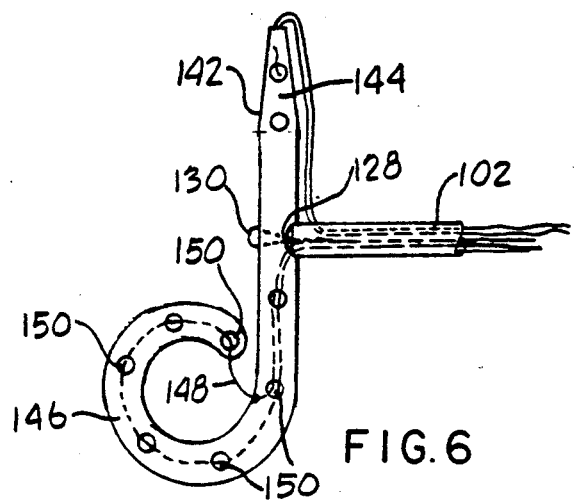
FIG. 6
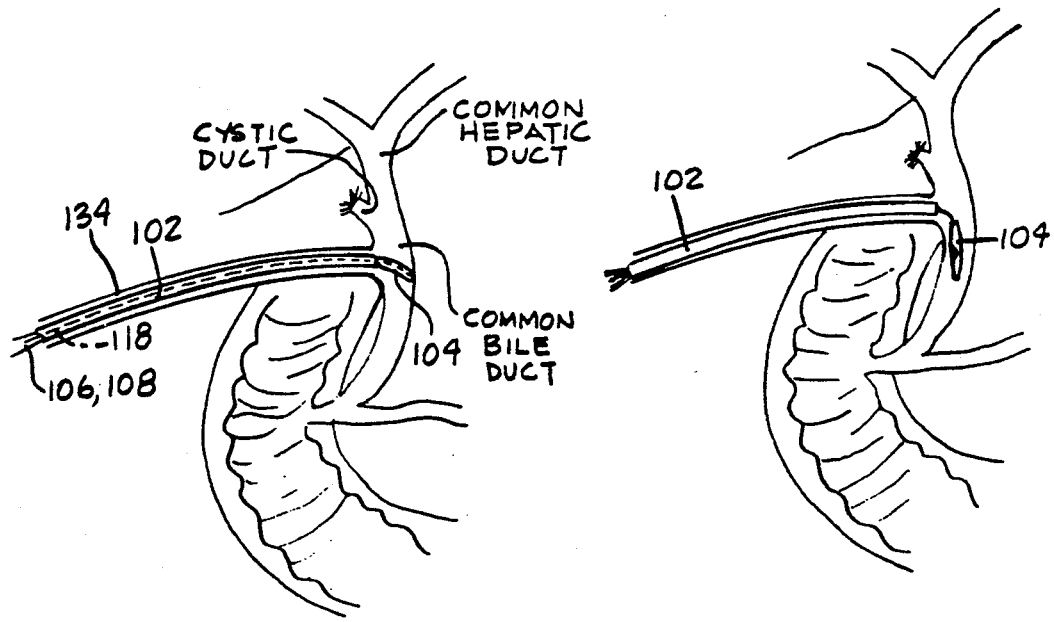
FIG. 8A
FIG. 8B

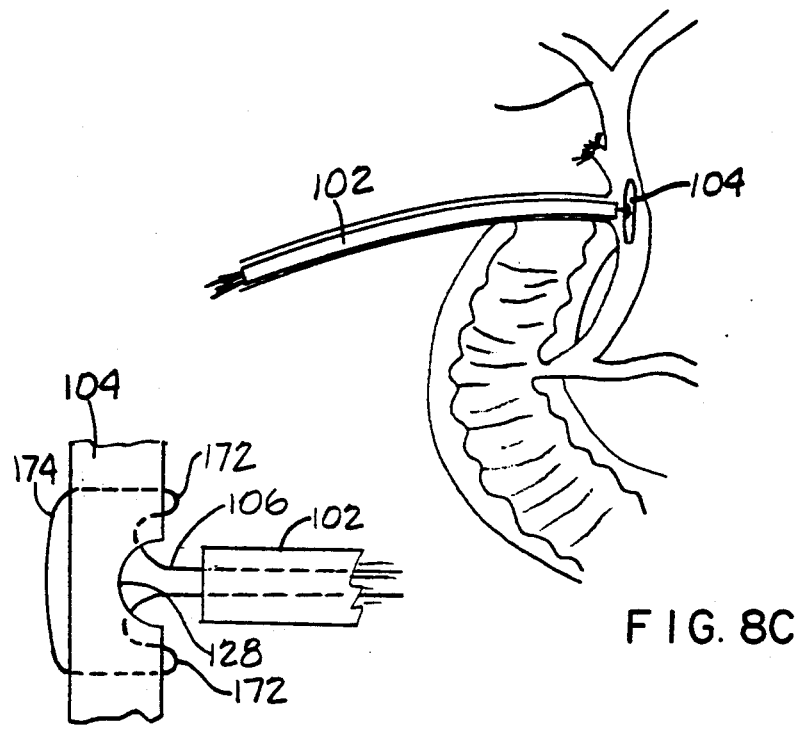
FIG. 8C
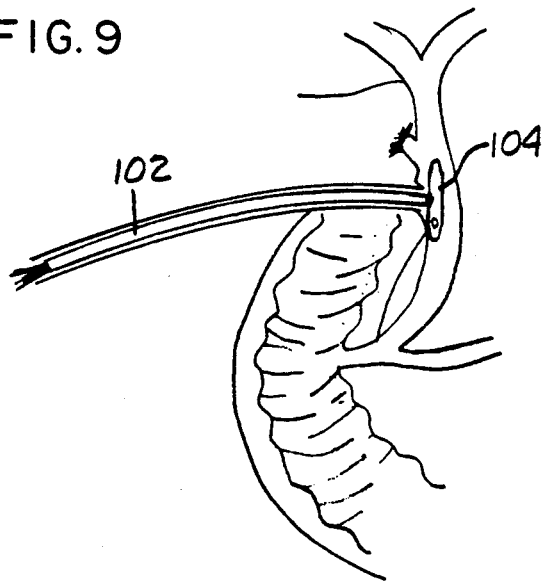
FIG. 9
FIG. 8D
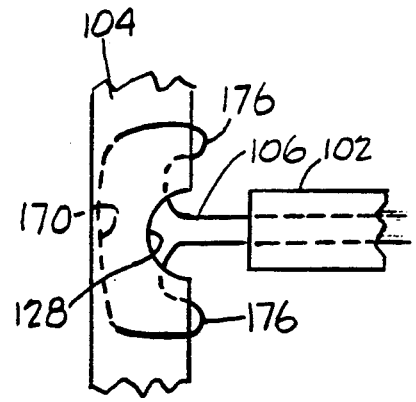
FIG. 10

TWO-PIECE RETRIEVABLE CATHETER FORMING STRAIGHT AND T-SHAPE CONFIGURATIONS

BACKGROUND OF THE INVENTION

The present invention relates in general to a surgical accessory, and more particularly, to a two-piece retrievable catheter for replacement of a dislodged T-tube previously surgically implanted in the internal ducts or vessels of a patient as a conduit to stent and/or provide drainage after a surgical procedure, for example, the common bile duct following surgery to remove gallstones or the gallbladder itself.

The surgical implantation of a T-tube following surgery, in particular, open cholecystectomy, is well-known in the medical field as well as the patent literature. Typically, these T-tubes are made from a highly flexible material so that when their function is no longer needed, they may be removed by simply pulling them out of the patient. For example, Goldberg et al., U.S. Pat. No. 3,835,863, discloses a flexible T-tube which is surgically implanted in an internal duct or vessel of a patient in order to facilitate the removal of the T-tube when it is no longer needed. The T-tube includes a continuous slit extending longitudinally across the top of the cross tube. As the T-tube is pulled out from the patient for removal, the longitudinal slit causes the arms of the cross tube to telescope within each other to form a smaller cross-section which minimizes the amount of trauma and stress in the duct. T-tubes without a slit are known from Morales-George, U.S. Pat. No. 4,654,032 and Whelan, Jr., U.S. Pat. No. 4,142,528.

Hartenbach, U.S. Pat. No. 3,833,940 discloses a metal or plastic cannula which is surgically implanted in the bile duct of the patient. A radially extending nipple in communication with the interior of the cannula protects against the longitudinal displacement of the cannula and permits a drainage hose to be connected thereto. Optionally, one or both of the end sections of the cannula may be detachable from the nipple portion, thereby making the implantation of the cannula within a bile duct easier.

Swartz, U.S. Pat. No. 4,072,153, discloses a flexible T-tube for use as a fluid drainage tube following a hysterectomy. A large central drain port formed at the intersection of the cross tube and drain tube causes the arms of the cross tube to fold up on one another as the drain tube is pulled, thereby facilitating the withdrawal of the tube from the patient.

Jones, U.S. Pat. No. 4,248,224, discloses a double lumen flexible catheter having a generally Y or T shape formed at a distal end. A substantially stiff sleeve is slidably fitted over the cannula. As the sleeve is slid over the lower branch portions at the distal end of the catheter, it urges the branch members into alignment with the upper fluid conveying tube so the entire structure can be passed through a relatively small single surgical opening. Once properly positioned, the sleeve can be retracted so that the two branch members return to their Y or T configuration within the duct.

Grunwald, U.S. Pat. No. 4,309,994, discloses a flexible Y or T shaped cannula which is similar to that of Jones. The divergent ends of the cannula are straightened for insertion into the vena cavae of a patient by an elongated obturator slidably inserted therein. The obturator includes a straight body having two straight branches extending from one end thereof. As the obturator is slid into the cannula, the branches engage and straighten the branches of the cannula to facilitate the insertion of same into the vena cavae through a single surgical opening. Upon withdrawal of the obturator, the branches of the cannula will return to their normal Y or T configuration.

Patel, U.S. Pat. No. 4,748,984 discloses a catheter assembly for use in performing coronary angiography and angioplasty. The catheter consists of an elongate guiding portion having a tip portion pivotally connected thereto. A guide wire inserted into the guiding catheter and tip portion maintains these elements in alignment as the assembly is inserted into the patient's aorta. The guide wire is then removed and the guiding catheter maneuvered until the tip portion pivots to a position adjacent the tip of the guiding catheter. In addition, the tip portion of the catheter may be curved to form a loop.

In addition to the T-tube, it is also known that catheters having a straight configuration may be inserted into a patient over a guide wire. Once inserted, the guide wire is removed, and by pulling on a suture or series of sutures threaded therethrough, the tip of the catheter may be curled to form a loop or S-shape. When the catheter is no longer needed, the tension on the suture is relieved and the guide wire reinserted, thereby straightening the catheter for removal.

Despite these known medical devices and surgical procedures, replacement of a dislodged T-tube may be impossible or difficult, at best. Reinsertion of a soft surgical T-tube requires folding of the trailing limb and this doubled tubing may not pass through the undilated or tortuous T-tube tract. If the T-tube is dislodged early in the post-operative period, replacement may result in tract perforation and peritonitis. When retained common bile duct stones or obstructions from sticture or neoplasm are present, T-tube replacement is mandatory. If a T-tube cannot be replaced, biliary drainage catheters can be used, but these may leak, drain poorly or become malpositioned. Accordingly, there is an unsolved need for a T-tube catheter which can easily be placed percutaneously within a patient for replacement of a dislodged T-tube, particularly during the post-operative period.

SUMMARY OF THE INVENTION

A retrievable T-tube catheter has been developed in accordance with the present invention for easy insertion into the common bile duct. The T-tube catheter has a two piece design, but is introduced as a single unit over an introducer cannula and guide wire. The T-tube catheter is then formed upon removal of the guide wire and cannula in-situ within the common bile duct. A suture-locking device affords self-retaining characteristics and the T-tube catheter can be easily retrieved, repositioned or exchanged. The T-tube catheter can be modified within a long distal limb to stent the Ampulla of Vater after balloon sphincteroplasty. Alternatively, a second type of catheter with a self-retaining loop can be used as an internal biliary drainage catheter when treating distal common bile duct obstruction. This T-loop catheter is inserted through the T-tube tract and avoids placement of a transhepatic catheter.

In the present invention, an elongated main catheter and a separate and distinct auxiliary catheter are assembled in axial alignment over a cannula for insertion into the common bile duct or similar vessel or canal within the patient. Two sutures threaded through the main catheter are attached to the auxiliary catheter, one in the center of the auxiliary catheter and one at an end thereof. After the two piece catheter has been inserted to the desired location and the cannula removed, the sutures are manipulated to maneuver the auxiliary catheter until it lies perpendicularly to the elongated main catheter to thereby form a T-tube.

For removal of the catheter from the patient through the T-tube track, the sutures are once again manipulated to align the auxiliary catheter with the elongated main catheter. The cannula is then inserted through both the elongated main and auxiliary catheters and the entire assembly is removed together. Both the insertion and removal procedures are performed with the aid of an X-ray television to assure that the elongated main and auxiliary catheters are properly aligned. Not only may the present invention be used for the in-situ formation of T-tubes but, with the proper arrangement of sutures, T-loops may be formed in-situ as well.

In accordance with one embodiment of the present invention, there is disclosed a two piece retrievable catheter for insertion into the duct of a patient to provide a conduit from inside the duct to outside the body wall of the patient. The catheter is constructed of a first catheter portion a second catheter portion, and connecting means for connecting the first catheter portion to the second catheter portion in two different configurations upon manipulation of the connecting means while the second catheter portion is positioned within the duct, the second catheter portion providing fluid communication between the duct and the first catheter portion when arranged in at least one of the two different configurations.

In accordance with another embodiment of the present invention, there is disclosed a two piece retrievable catheter for insertion into the common bile duct of a patient to provide a conduit from inside the duct to outside the body wall of the patient. The catheter is constructed of a main catheter, an auxiliary catheter, and connecting means for connecting the main catheter to the auxiliary catheter upon manipulation of the connecting means. The manipulation of the connecting means arranges the auxiliary catheter between a first position in longitudinal alignment with the main catheter for insertion of the catheter into the common bile duct and a second position in angular relationship with the main catheter for fluid communication with the common bile duct.

BRIEF DESCRIPTION OF THE DRAWINGS

The above description, as well as further objects, features and advantages of the present invention will be more fully understood with reference to the following detailed description of a two-piece retrievable catheter, when taken in conjunction with the accompanying drawings, wherein:

FIGS. 4A-4D are side elevational views showing alternative construction features for uniting the two-piece retrievable catheter to form the T-limb as shown in FIG. 3;

FIG. 6 is a side elevational view of the auxiliary catheter of the two-piece retrievable catheter forming a T-loop in accordance with another embodiment of the present invention;

FIGS. 8(a)-(d) is a diagrammatic illustration showing replacement of a dislodged previously surgically inserted T-tube with the two-piece retrievable catheter of the present invention into the common bile duct of a patient;

FIG. 9 is a side elevational view of another embodiment of attaching the auxiliary catheter to a suture for manipulation to form the T-limb; and FIG. 10 is a side elevational view of another embodiment of attaching the auxiliary catheter to a suture for manipulation to form the T-limb.

DETAILED DESCRIPTION

Figure 1:
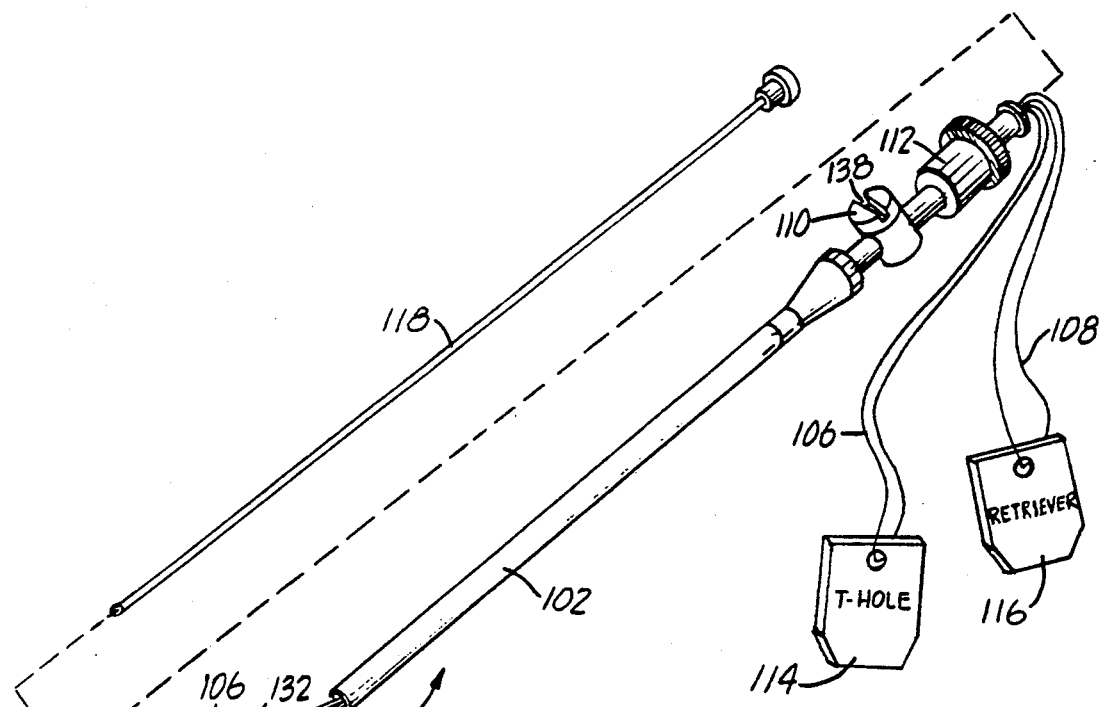
FIG. 1 is a perspective view of a two-piece retrievable catheter constructed in accordance with one embodiment of the present invention.

Referring now to the drawings, wherein like reference numerals represent like elements, there is shown in FIG. 1 a two-piece retrievable catheter constructed in accordance with the present invention and generally designated by reference numeral 100. The catheter 100 includes a single lumen flexible main catheter 102 and a flexible single lumen or T-limb auxiliary catheter 104 operatively connected by sutures 106, 108. The proximal portion of the main catheter 102 includes a conventional locking valve 110 and an enlargement 112 in the nature of a female valve which may also function as a handle for manipulation of the catheter 100. The locking valve is one obtainable from Medi-tech of Watertown, Mass. The sutures 106, 108 extend from the auxiliary catheter 104, through the single lumen of the main catheter 102, through the locking valve 110 and enlargement 112, and are secured at their free end to a respective flat paddle 114, 116. To facilitate insertion of the catheter 100, there is provided a stiffer, yet flexible hollow cannula 118 dimensioned to receive a guide wire and to be slidingly received through the interior of the main catheter 102 and auxiliary catheter 104.

The main catheter 102 generally has a uniform cylindrical cross-section along its length. On the other hand, the auxiliary catheter 104 includes a center portion 120 of generally uniform cylindrical cross-section extending between a pair of gradually tapered ends 122, 124. However, the auxiliary catheter 104 may also be of uniform cross-section along its length. The auxiliary catheter 104 is provided with a plurality of openings 126 and a centrally arranged T-hole 28. The tapered ends 122, 124 may be of different length, in particular, whereby the T-hole is not centered within the auxiliary catheter 104. Suture 106 is attached to the side wall of the auxiliary catheter 104 by passing through the T-hole 128 and looping through a pair of spaced apart pin holes (not shown) in the auxiliary catheter side wall to form a taunt loop 130. The pin holes are spaced apart slightly wider than the diameter of the T-hole 128. Suture 108 is attached to the tapered end 124 of the auxiliary catheter 104 by passing from the interior thereof through opening 126 and back to the interior through a pinhole (not shown) in the side wall of the tapered end to form a taunt loop 132.

Figure 2:
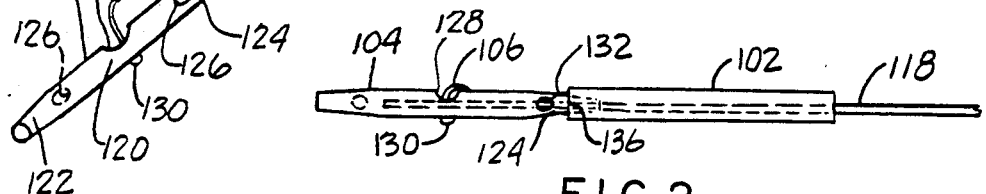
FIG. 2 is a side elevational view of the distal portion of the two-piece retrievable catheter shown in arrangement for insertion into the patient such as the common bile duct.
Figure 3:
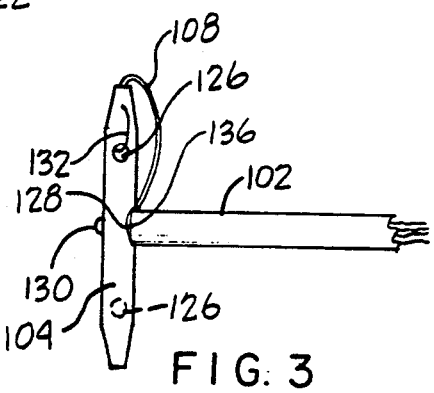
FIG. 3 is a side elevational view of the distal portion of the two-piece retrievable catheter which has been manipulated in-situ after insertion into the patient to form a T-limb.

The percutaneous introduction of the two-piece retrievable catheter 100 for the replacement of a dislodged surgically implanted T-tube will now be described with respect to FIGS. 2, 3 and 8. The catheter 100 is initially assembled for placement into the previously prepared T-tube track 134 by pulling suture 108 taunt by means of paddle 116. As shown in FIG. 2, the auxiliary catheter 104 is arranged in longitudinal alignment with the main catheter 102 with the tapered end 124 engaged with the mouth 136 of the main catheter. This arrangement of the main catheter 102 and auxiliary catheter 104 is maintained by securing the sutures 106, 108 by rotating the locking valve 110 180° using one of the paddles 114, 116 which are sized to engage the notch 138 provided on the internal hub (not shown) of the locking device. Upon rotation of the hub, the sutures 106, 108 are wrapped thereabout to secure same in a taunt condition while maintaining fluid communication between the main catheter 102 and the enlargement 112.

The main catheter 102 and auxiliary catheter 104 are stiffened to facilitate introduction by insertion of the cannula 118 through their respective hollow interiors as shown in FIG. 2. The catheter 100 is gently advanced and manipulated through the T-tube track 134 over a guide wire (not shown) until the auxiliary catheter 104 is positioned within the common bile duct as shown in FIG. 8A. The guide wire and cannula 118 are removed and the locking valve 110 rotated to release sutures 106, 108 allowing separation of the auxiliary catheter 104 from the main catheter 102 as shown in FIG. 8B. The T-hole paddle 114 is pulled causing the auxiliary catheter 104 to orient itself with its longitudinal axis approximately perpendicular to the longitudinal axis of the main catheter 102 as shown in FIG. 8C, although outer angular relationships are possible. The pulling of the T-hole suture 106 to a taunt condition will secure the auxiliary catheter in angular relationship to the main catheter 102 with the mouth 136 of the main catheter being received within or engaging the T-hole 128 of the auxiliary catheter as best shown in FIG. 3, as well as FIG. 8D. The main catheter 102 is now in fluid communication with the common bile duct through the auxiliary catheter 104. This arrangement of the main catheter 102 and auxiliary catheter 104 is maintained by placing the T-hole suture 106 in a taunt condition by securing same by means of the locking valve 110 as previously described.

One application of the catheter 100 in accordance with the present invention is for drainage of the common bile duct following surgery performed on the gallbladder such as its removal. The catheter 100 can also be utilized to flush the common bile duct or for other purposes while still inserted therein, such as the nonsurgical removal of retained stones and the like from the duct to a location outside the body wall of the patient. The catheter 100 may also be used to infuse medication to dissolve the stones, as well as providing access to other internal blockages such as at the Ampulla of Vater, to stent intra hepatic obstructions, to drain bile externally and to stent or protect a duct that had been opened or dilated. In this regard, the auxiliary catheter 104 may be modified to have one tapered end 122, 124 of sufficient length to stent the Ampulla of Vater after balloon sphincteroplasty. In addition, upon laproscopic gallbladder removal or open cholecystectomy, the catheter 100 may be placed within the cystic duct and the auxiliary catheter 104 arranged bridging the common hepatic duct and common bile duct to withdraw bile fluid, remove stones and to dilate narrow passages while keeping the ducts patent. The catheter 100 may be removed from the body of the patient by reversing the above-described procedure.

Referring now to FIGS. 4A–4D, there is disclosed various embodiments of the joining of the mouth 136 of the main catheter 102 to the T-hole 128 of the auxiliary catheter 104. In FIG. 4A, the main catheter 102 is provided with a blunt mouth 136 to engage a circular T-hole 128 within the auxiliary catheter 104. In FIG. 4B, the mouth 136 of the main catheter 102 has been rounded to provide a better conforming fit with the T-hole 128 which has been formed with tapered side walls as indicated by the dashed lines. In FIG. 4C, the T-hole 128 has a square shape to engage in a more conforming fit with the blunt mouth 136 of the main catheter 102. In FIG. 4D, the mouth 136 of the main catheter 102 has been tapered to engage the T-hole 128 which has been formed by tapered side walls of the auxiliary catheter 104 as indicated by the dashed lines. It is to be understood that it is not a requirement that a fluid tight seal be created between the mouth 136 of the main catheter 102 and the T-hole 128 of the auxiliary catheter 104. In this regard, bile from the common bile duct will take the path of least resistance. In the event of blockage of the common bile duct below the position of the auxiliary catheter 104, the bile will back up and flow outside the patient's body through the catheter 100 irrespective of providing a fluid tight seal between the mouth 136 of the main catheter and T-hole 128 of the auxiliary catheter.

Figure 5:
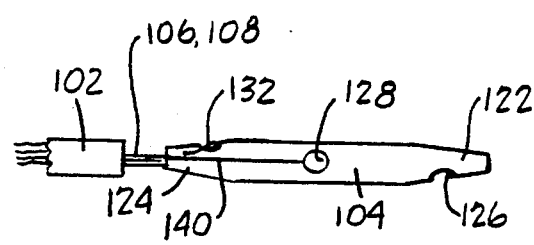
FIG. 5 is a side elevational view of the auxiliary catheter of the two-piece retrievable catheter in accordance with another embodiment of the present invention.

The auxiliary catheter 104 can also be constructed in accordance with the embodiment disclosed in FIG. 5. As shown, the auxiliary catheter 104 is provided with a longitudinal slit 140 within its side wall extending from the T-hole 128 to the edge of the tapered end 124. The slit 140 enables the T-hole suture 106 to be received within the hollow interior of the auxiliary catheter 104 as opposed to being exposed as shown in FIG. 1. As the auxiliary catheter 104 is being manipulated from its position shown in FIG. 8A to its position shown in FIG. 8D, the T-hole suture 106 slides through the slit 140 from the tapered end 124 until it reaches the T-hole 128. One advantage of the auxiliary catheter 104 in accordance with the FIG. 5 embodiment, is the maintaining of the T-hole suture 106 inside the auxiliary catheter 104 during placement. This arrangement may facilitate placement of the auxiliary catheter 104 under certain conditions where obstructions or narrow passages are encountered. However, the auxiliary catheter 104 constructed in accordance with the FIG. 1 embodiment is preferred as it possess greater mechanical strength as a result of the absence of the slit 140.

Referring to FIG. 6, another embodiment of an auxiliary catheter 142 is shown in the nature of a T-loop. The auxiliary catheter 142 is provided with a short catheter segment 144 and a lengthened catheter segment 146. A loop suture 148 extends from T-hole 128, through lengthened catheter segment 146, out on opening 150 at the end of the lengthened catheter segment and through a pinhole (not shown) remote therefrom formed in the side wall of the lengthened catheter segment. The loop suture 148 returns through the T-hole 128 and through the main catheter 102 to an additional paddle (not shown). The lengthened catheter segment 146 is initially arranged in longitudinal alignment with the short catheter segment 144 for placement within the common bile duct. After arrangement of the auxiliary catheter 142 in its generally perpendicular or other angular relationship with the main catheter 102 as previously described, the loop suture 148 is brought into a taunt condition by pulling the additional paddle to form a substantially closed loop. The resulting loop provides the catheter 100 with greater retentive ability within the common bile duct which is particularly useful in obese patients.

Figure 7:
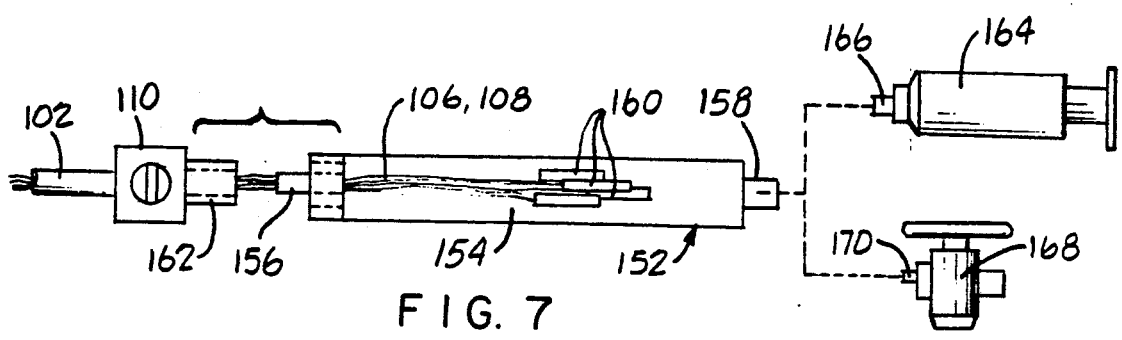
FIG. 7 is a side elevational view of the proximal portion of the two-piece retrievable catheter in accordance with another embodiment of the present invention including a detachable suture storage device.

The paddles 114, 116 as shown in FIG. 1 extend hanging exterior to the catheter 100 and outside the body of the patient which might be considered an inconvenience. Referring to FIG. 7, there is shown a suture storage device 152 which also functions as a flush extension tube. The suture storage device 152 is constructed from a cylindrical hollow tube 154 having a male luer connection 156 at one end and a female luer connection 158 at the other. The sutures 106, 108 extend into the interior of the hollow tube 154 for storage and are terminated by metal elongated handles 160 as opposed to the previously described paddles 114, 116. The handles 160 are sized to pass through the male or female luer connections 156, 158 for use. The suture storage device 152 is connectable to the proximal portion of the catheter 100 by means of a female luer connection 162 attached to the locking valve 110. It should be appreciated that other forms of connection between the suture storage device 152 and the catheter 100 may be used.

In addition to the suture storage device 152 functioning to store the sutures 106, 108, the device may function as a flush extension tube. In this regard, a syringe 164 having a male luer connection 166 may be used for injecting medicine, flushing fluids and the like through the suture storage device 152 upon connection to the female luer connection 158. In addition, a stop cock 168 having a male luer connection 170 may be attached to the female luer connector 158 of the suture storage device 152.

Referring to FIGS. 9 and 10, two additional embodiments for attaching the T-hole suture 106 to the auxiliary catheter 104 are disclosed. As shown in FIG. 9, the T-hole suture 106 passes through the T-hole 128 and through a plurality of pinholes (not shown) within the side wall of the auxiliary catheter 104 in the manner shown. In particular, the T-hole suture 106 forms an outer loop 172 on either side of the T-hole 128 as the suture passes through the sidewall of the auxiliary catheter 104. The T-hole suture 106 continues through the interior of the auxiliary catheter 104 and outwardly through a pair of spaced-apart pinholes (not shown) to form an outer loop 174 opposite the T-hole 128.

In the embodiment shown in FIG. 10, the T-hole suture 106 also forms an outer loop 176 on either side of the T-hole 128. As shown, the outer loop 176 has a greater length than the outer loop 172 shown in FIG. 9. The greater length of the outer loop 176 is achieved by passing the T-hole suture 106 through the sidewall of the auxiliary catheter 104 at a location further removed from the initial exit pinhole than that as previously described with respect to FIG. 9. The T-hole suture 106 forms an inner loop 178 opposite the T-hole 128 within the interior of the auxiliary catheter 104 as indicated by the dashed lines. These latter two embodiments for attaching the T-hole suture 106 to the auxiliary catheter 104 are contemplated as providing a more stable and secure attachment of the auxiliary catheter to the main catheter 102 at the desired angular relationship over the previously described embodiment with respect to FIG. 1.

Although the invention herein has been described with references to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

I claim:

1. A connectable two piece retrievable catheter for insertion into the duct of a patient to provide a conduit from inside the duct to outside the body wall of the patient, said catheter comprising a first catheter piece, a second catheter piece releasably connectable to said first catheter piece, and connecting means attached to said second catheter piece for connecting said second catheter piece to said first catheter piece in different first and second configurations upon manipulation of said connecting means while said second catheter piece is positioned within said duct, said second catheter piece connected in longitudinal alignment with said first catheter piece when in said first configuration and in transverse relationship with said first catheter piece when in said second configuration, said second catheter piece having fluid communication means providing fluid communication between said duct and said first catheter piece when arranged in at least said second configuration.

2. The catheter of claim 1, wherein said first catheter piece comprises an elongated main catheter and said second catheter piece comprises an elongated auxiliary catheter of shorter length than said main catheter.

3. The catheter of claim 1, further including means for altering the shape of a portion of said second catheter piece from a straight configuration to a loop configuration.

4. The catheter of claim 1, further including storage means connectable to the proximal end of said first catheter piece for storage of a portion of said connecting means, said storage means arranged in fluid communication with said first catheter piece.

5. The catheter of claim 1, wherein said connecting means comprises a pair of sutures.

6. The catheter of claim 5, wherein the manipulation of one of said sutures configures said first catheter piece and said second catheter piece in said longitudinal alignment and in fluid communication with each other.

7. The catheter of claim 6, wherein the manipulation of another of said sutures configures said second catheter piece in said transverse relationship to said first catheter piece and in fluid communication with each other.

8. The catheter of claim 7, further including locking means for locking said sutures to maintain the configuration of said first catheter piece with respect to said second catheter piece.

9. The catheter of claim 7, wherein said fluid communication means includes a hole along the length of said second catheter piece for receiving an end of said first catheter piece when arranged in said transverse relationship to maintain fluid communication therebetween.

10. The catheter of claim 9, wherein said one of said sutures is attached to one end of said second catheter piece and said another of said sutures extends through said hole and is attached to said second catheter piece at a location opposite said hole.

11. The catheter of claim 9, wherein said hole is arranged off center along the length of said second catheter piece.

12. The catheter of claim 9, further including a slit formed in said second catheter piece extending from said hold to one end of said second catheter piece.

13. A two piece retrievable catheter for insertion into the common bile duct of a patient to provide a conduit from inside the duct to outside the body wall of the patient, said catheter comprising a main catheter, an auxiliary catheter, and connecting means attached to said auxiliary catheter for connecting said auxiliary catheter to said main catheter upon manipulation of said connecting means, said manipulation of said connecting means arranging said auxiliary catheter between a first position in longitudinal alignment with said main character for insertion of said catheter into said common bile duct and a second position in angular relationship with said main catheter for fluid communication with said common bile duct, said auxiliary catheter including a hole along the length thereof for receiving an end of said main catheter when arranged in said angular relationship to maintain fluid communication therebetween.

14. The catheter of claim 13, further including means for altering the shape of a portion of said auxiliary catheter from a straight configuration to a loop configuration.

15. The catheter of claim 13, further including storage means connectable to the proximal end of said main catheter for storage of a portion of said connecting means, said storage means arranged in fluid communication with said main catheter.

16. The catheter of claim 13, further included a cannula receivable within said main catheter and said auxiliary catheter to facilitate the insertion thereof within said patient.

17. The catheter of claim 13, wherein said connecting means comprises a pair of sutures attached to said auxiliary catheter.

18. The catheter of claim 17, further including locking means for locking said sutures to maintain said position of said main catheter with respect to said auxiliary catheter.

19. The catheter of claim 17, wherein said angular relationship comprises a generally perpendicular relationship.

20. The catheter of claim 17, wherein said main catheter and said auxiliary catheter each include a passageway extending therethrough.

21. The catheter of claim 20, wherein one of said sutures is attached to one end of said auxiliary catheter and another of said sutures extends through said hole and is attached to said auxiliary catheter at a location opposite said hole.

22. The catheter of claim 20, wherein said hole is arranged off center along the length of said auxiliary catheter.

23. The catheter of claim 20, further including a slit formed in said auxiliary catheter extending from said hole to one end of said auxiliary catheter.

24. The catheter of claim 20, wherein one of said sutures extends into said hole, and extends at a plurality of locations through the sidewall forming said auxiliary catheter to form an outer loop on either side of said hole and an outer loop opposite said hole.

25. The catheter of claim 20, wherein one of said sutures extends into said hole, and extends through the sidewall forming said auxiliary catheter at a plurality of locations to form an outer loop on either side of said hole and an inner loop opposite said hole.

26. A connectable two piece retrievable catheter for insertion into the duct of a patient to provide a conduit from inside the duct to outside the body wall of the patient, said catheter comprising a first catheter piece, a second catheter piece releasably connectable to said first catheter piece connecting means attached to said second catheter piece for connecting said second catheter piece to said first catheter piece in different first and second configurations upon manipulation of said connecting means while said second catheter piece is positioned within said duct, said second catheter piece connected in longitudinal alignment with said first catheter piece when in said first configuration and in angular relationship with said first catheter piece when in said second configuration, said second catheter piece having fluid communication means providing fluid communication between said duct and said first catheter piece when arranged in at least said second configuration and means for altering the shape of a piece of said second catheter piece from a straight configuration to a loop configuration.

27. A connectable two piece retrievable catheter for insertion into the duct of a patient to provide a conduit from inside the duct to outside the body wall of the patient, said catheter comprising a first catheter piece having an end opening, a second catheter piece releasably connectable to said first catheter piece, and connecting means attached to said second catheter piece for connecting said second catheter piece to said first catheter piece in different first and second configurations upon manipulation of said connecting means while said second catheter piece is positioned within said duct, said second catheter piece connected in longitudinal alignment with said first catheter piece when in said first configuration and in angular relationship with said first catheter piece when in said second configuration, said second catheter piece providing fluid communication between said duct and said first catheter piece when arranged in at least said second configuration, said second catheter piece including a hole along the length thereof for receiving said end opening of said first catheter piece when arranged in said angular relationship to maintain fluid communication therebetween.

28. A connectable two piece retrievable catheter for insertion into the duct of a patient to provide a conduit from inside the duct to outside the body wall of the patient, said catheter comprising a hollow first catheter piece having an end opening, a hollow second catheter piece releasably connectable to said first catheter piece having a side opening, a pair of sutures extending through said hollow first catheter piece and connected to said hollow second catheter piece, said hollow second catheter piece connected in end-to-end longitudinal alignment with said hollow first catheter piece upon manipulation of one of said sutures and connected at an angle to said first hollow catheter piece by said end opening of said hollow first catheter piece being retrieved within said side opening of said second catheter piece upon manipulation of another of said sutures to maintain fluid communication therebetween.

* * * * *

UNITED STATES PATENT AND TRADEMARK OFFICE
CERTIFICATE OF CORRECTION

PATENT NO.  : 5,213,575
DATED       : May 25, 1993
INVENTOR(S) : Daniel M. Scotti It is certified that error appears in the above-identified patent and that said Letters Patent is hereby corrected as shown below:

Column 6, line 64, "on" should read --one--.
Column 9, line 21, "character" should read --catheter--.
Column 10, line 64, "retrieved" should read --received--.

Signed and Sealed this

First Day of February, 1994

Attest:

BRUCE LEHMAN

Attesting Officer          Commissioner of Patents and Trademarks